US012635907B2

(12) United States Patent
Delp et al.

(10) Patent No.: US 12,635,907 B2
(45) Date of Patent: May 26, 2026

(54) SYSTEM AND METHOD FOR AUTOMATIC EVALUATION OF GAIT USING SINGLE OR MULTI-CAMERA RECORDINGS

(71) Applicants: The Board of Trustees of the Leland Stanford Junior University, Stanford, CA (US); Gillette Children's Specialty Healthcare, St. Paul, MN (US)

(72) Inventors: Scott Delp, Stanford, CA (US); Lukasz Kidzinski, Menlo Park, CA (US); Bryan Yang, San Jose, CA (US); Michael Schwartz, Minneapolis, MN (US); Jennifer Lee Hicks, Fremont, CA (US)

(73) Assignees: The Board of Trustees of the Leland Stanford Junior University, Stanford, CA (US); Gillette Children's Specialty Healthcare, St. Paul, MN (US)

( * ) Notice: Subject to any disclaimer, the term of this patent is extended or adjusted under 35 U.S.C. 154(b) by 445 days.

(21) Appl. No.: 17/260,970

(22) PCT Filed: Jul. 15, 2019

(86) PCT No.: PCT/US2019/041896
§ 371 (c)(1),
(2) Date: Jan. 15, 2021

(87) PCT Pub. No.: WO2020/018469
PCT Pub. Date: Jan. 23, 2020

(65) Prior Publication Data
US 2021/0315486 A1 Oct. 14, 2021

Related U.S. Application Data

(60) Provisional application No. 62/698,725, filed on Jul. 16, 2018.

(51) Int. Cl.
*A61B 5/11* (2006.01)
*A61B 5/00* (2006.01)
(Continued)

(52) U.S. Cl.
CPC ............ *A61B 5/112* (2013.01); *A61B 5/1128* (2013.01); *A61B 5/4082* (2013.01);
(Continued)

(58) Field of Classification Search
CPC ..... A61B 5/112; A61B 5/1128; A61B 5/4082; A61B 5/7267; A61B 2576/00;
(Continued)

(56) References Cited

U.S. PATENT DOCUMENTS 7,257,237 B1 8/2007 Luck et al.
9,445,769 B2 9/2016 Ghassemzadeh et al.
(Continued)

FOREIGN PATENT DOCUMENTS

CA 2466210 C 1/2014
CN 111144217 A 5/2020
(Continued)

OTHER PUBLICATIONS

International Search Report and Written Opinion for International Application No. PCT/US2019/041896, Search completed Sep. 17, 2019, Mailed Oct. 2, 2019, 13 Pgs.
(Continued)

*Primary Examiner* — Tse W Chen
*Assistant Examiner* — Evelyn Grace Park
(74) *Attorney, Agent, or Firm* — KPPB LLP

(57) ABSTRACT

Systems and methods in accordance with many embodiments of the invention include a motion evaluation system that trains a model to evaluate motion (such as, but not limited to, gait) through images (or video) captured by a single image capture device. In certain embodiments,
(Continued)

motion evaluation includes predicting clinically relevant variables from videos of patients walking from keypoint trajectories extracted from the captured images.

18 Claims, 9 Drawing Sheets

(51) Int. Cl.
| | |
|---|---|
| *G16H 50/20* | (2018.01) |
| *G16H 50/30* | (2018.01) |
| *G16H 50/50* | (2018.01) |

(52) U.S. Cl.
CPC .......... *A61B 5/7267* (2013.01); *G16H 50/20* (2018.01); *G16H 50/30* (2018.01); *G16H 50/50* (2018.01); *A61B 2576/00* (2013.01)

(58) Field of Classification Search
CPC ........ G16H 50/20; G16H 50/30; G16H 50/50; G06V 40/25; G06V 40/00
See application file for complete search history.

(56) References Cited

U.S. PATENT DOCUMENTS

| | | | |
|---|---|---|---|
| 9,604,142 B2 | 3/2017 | Bentley et al. | |
| 9,700,241 B2 | 7/2017 | Eastman et al. | |
| 9,811,720 B2 | 11/2017 | Zhong | |
| 2007/0229522 A1 | 10/2007 | Wang et al. | |
| 2012/0253201 A1 | 10/2012 | Reinhold | |
| 2015/0106024 A1* | 4/2015 | Lightcap | A61B 5/4851 |
| | | | 600/587 |
| 2017/0000386 A1 | 1/2017 | Salamatian et al. | |
| 2018/0020954 A1 | 1/2018 | Lillie et al. | |
| 2019/0110736 A1* | 4/2019 | Broderick | G06T 7/246 |
| 2019/0110754 A1* | 4/2019 | Rao | G06N 7/00 |
| 2021/0307621 A1* | 10/2021 | Svenson | A61B 5/015 |

FOREIGN PATENT DOCUMENTS

| | | |
|---|---|---|
| CN | 110458046 B | 11/2020 |
| TW | 202016691 A | 5/2020 |
| WO | 2020018469 A1 | 1/2020 |

OTHER PUBLICATIONS

"Gait Analysis", UnitedHeatlhcare Commercial Medical Policy, May 1, 2017, 9 pgs.

Balazia et al., "Gait Recognition from Motion Capture Data", ACM Transactions on Multimedia Computing, Communications, and Applications, vol. 1, No. 1, Oct. 2017, 18 pgs., https://doi.org/10.1145/nnnnnnn.nnnnnnn.

Balazia et al., "Learning Robust Features for Gait Recognition by Maximum Margin Criterion", Proceedings of the 23rd International Conference on Pattern Recognition, Cancun, Mexico, Dec. 4-8, 2016, 6 pgs., arXiv:1609.04392, Aug. 24, 2017.

Benndorf et al., "Automated Annotation of Sensor data for Activity Recognition using Deep Learning", INFORMATIK 2017, Gesellschaft fur Informatik, Bonn 2017, pp. 2211-2219, doi:10.18420/in2017_220.

Cao et al., "Realtime Multi-Person 2D Pose Estimation using Part Affinity Fields", arXiv:1611.08050v2 [cs.CV], Apr. 14, 2017, 9 pgs.

Castelli et al., "A 2D Markerless Gait Analysis Methodology: Validation on Healthy Subjects", Hindawi Publishing Corporation, Computational and Mathematical Methods in Medicine, vol. 2015, No. 186780, 11 pgs., http://dx.doi/10.1155/2015/186780.

Castro et al., "Evaluation of CNN Architectures for Gait Recognition Based on Optical Flow Maps", Proceedings of the International Conference of the Biometrics Special Interest Group (BIOSIG), Darmstadt, Germany, Sep. 20-22, 2017, 9 pgs.

Chau, "A review of analytical techniques for gait data. Part 2: neural network and wavelet methods", Gait & Posture, vol. 13, Apr. 2001, pp. 102-120.

Crabbe et al., "Skeleton-Free Body Pose Estimation from Depth Images for Movement Analysis", Proceedings of the IEEE International Conference on Computer Vision Workshop (ICCVW), Santiago, Chile, Dec. 7-13, 2015, pp. 70-78.

Dehzangi et al., "IMU-Based Gait Recognition Using Convolutional Neural Networks and Multi-Sensor Fusion", Sensors, vol. 17, No. 12, Nov. 27, 2017, 22 pgs., doi:10.3390/d17122735.

Devanne et al., "Learning Shape Variations of Motion Trajectories for Gait Analysis", Proceedings of the 23rd International Conference on Pattern Recognition (ICPR), Cancun, Mexico, Dec. 4-8, 2016, pp. 895-900, doi:10.1109/ICPR.2016.7899749.

Feng et al., "Learning Effective Gait Features Using LSTM", Proceedings of the 23rd International Conference on Pattern Recognition (ICPR), Cancun, Mexico, Dec. 4-8, 2016, pp. 320-325.

Goffredo et al., "2D Markerless Gait Analysis", Proceedings of the 4th European Conference of the International Federation for Medical and Biological Engineering, vol. 22, 2008, pp. 67-71.

Hamill et al., "Read a Chapter on Angular Kinematics", Angular Kinematics, 20 pgs.

Hinton et al., "Lecture 6", Neural Networks for Machine Learning, Lecture 6A-6E, 31 pgs.

Kaczmarczyk et al., "Artificial Neural Networks (ANN) Applied for Gait Classification and Physiotherapy Monitoring in Post Stroke Patients", InTech, Chapter 16 of Artificial Neural Networks—Methodological Advances and Biomedical Applications, Apr. 11, 2011, pp. 303-328.

Ke et al., "A New Representation of Skeleton Sequences for 3D Action Recognition", arXiv:1703.03492v3 [cs.CV], Jun. 5, 2017, 10 pgs.

Li et al., "Skeleton-based Action Recognition Using LSTM and CNN", arXiv:1707.02356v1 [cs.CV], Jul. 6, 2017, 6 pgs.

Liu et al., "Learning Efficient Spatial-Temporal Gait Features with Deep Learning for Human Identification", Neuroinformatics, Oct. 2018, vol. 16, No. 3-4, Online Publication: Feb. 6, 2018, pp. 457-471, https://doi.org/10.1007/s12021-018-9362-4.

Mallick, "Deep Learning based Human Pose Estimation using OpenCV (C++ / Python)", IEEE Transactions on Computing, May 29, 2018, vol. 58, No. 10, pp. 1-12.

Maudsley-Barton et al., "A Comparative Study of the Clinical use of Motion Analysis from Kinect Skeleton Data", arXiv:1707.08813v2 [cs.CV], Jul. 31, 2017, 6 pgs.

Paiement et al., "Online quality assessment of human movement from skeleton data", In Proceedings British Machine Vision Conference, Sep. 2014, 12 pgs.

Sokolova et al., "Gait Recognition Based on Convolutional Neural Networks", The International Archives of the Photogrammetry, Remote Sensing and Spatial Information Sciences, vol. XLII-2/W4, 2017, pp. 207-212, doi:10.5194/isprs-archives-XLII-2-W4-207-2017.

Sokolova et al., "Pose-based Deep Gait Recognition", arXiv:1710.06512v3 [cs.CV], Feb. 8, 2018, 10 pgs.

Speciali et al., "Use of the Gait Deviation Index and spatiotemporal variables for the assessment of dual task interference paradigm", Journal of Bodywork and Movement Therapies, vol. 17, No. 1, Jan. 2013, pp. 19-27.

Tanawongsuwan et al., "Gait Recognition from Time-normalized Joint-angle Trajectories in the Walking Plane", Proceedings of the IEEE Computer Society Conference on Computer Vision and Pattern Recognition, Kauai, Hawaii, Dec. 8-14, 2001, 6 pgs.

Zadeh et al., "Abnormal Walking Gait Analysis Using neural network", Australian Journal of Basic and Applied Sciences, vol. 5, No. 9, Sep. 2011, pp. 1381-1390.

International Preliminary Report on Patentability for International Application PCT/US2019/041896, Issued on Jan. 19, 2021, Mailed on Jan. 28, 2021, 7 pages.

* cited by examiner

100

START

Train a model to evaluate joint position sequences    105

Extract joint position sequences from video    110

Generate evaluation scores to evaluate motion from the video    115

Provide outputs based on generated scores    120

END

900

SYSTEM AND METHOD FOR AUTOMATIC EVALUATION OF GAIT USING SINGLE OR MULTI-CAMERA RECORDINGS

CROSS-REFERENCE TO RELATED APPLICATIONS

The current application is a U.S. national phase of PCT Application No. PCT/US2019/041896 entitled, "System and Method for Automatic Evaluation of Gait Using Single or Multi-Camera Recordings", filed Jul. 15, 2019, which claims the benefit of and priority under 35 U.S.C. § 119(e) to U.S. Provisional Patent Application No. 62/698,725 entitled "System and Method for Automatic Evaluation of Gait Using Single or Multi-Camera Recordings" filed Jul. 16, 2018. The disclosures of PCT Application No. PCT/US2019/041896 and U.S. Provisional Patent Application No. 62/698,725 are hereby incorporated by reference in their entireties for all purposes.

STATEMENT OF FEDERAL SUPPORT

This invention was made with government support under contract EB020405 awarded by the National Institutes of Health. The government has certain rights in the invention.

FIELD OF THE INVENTION

The present invention generally relates to motion evaluation and, more specifically, the evaluation of motion using single or multi-camera recordings.

BACKGROUND

Many neurological and musculoskeletal diseases cause motion impairments that limit patient's function and social participation. Gait abnormality can suggest the presence of a number of pathologies, including Parkinson's disease, multiple sclerosis, cerebral palsy, stroke, osteoarthritis, and many other neurological or neuromuscular diseases or injuries. As such, being able to accurately detect deviations from normal gait in a patient is an important clinical task. Clinical gait analysis is a vital part of many orthopedic and neurological medical pipelines. Clinical gait analysis laboratories measure and analyze gait parameters to aid in surgical planning. To date, data is usually collected either by an optical motion capture system or by a physical therapist filling in a questionnaire. Optical motion capture assessment provides a wealth of quantitative information about gait, but is very expensive, requiring specialized equipment that can cost over $100 k, space in a clinic, and staff to operate the equipment (usually an engineer and a physical therapist). Data collection protocols often require positioning markers on the body of a patient and take over an hour to execute. With the current methods for gait analysis, patients must visit a clinical center, and the data collection capacity of a clinical center is severely limited. There is a great need for improved methods of gait analysis that can be performed at lower cost, in a shorter time, and in any location.

SUMMARY OF THE INVENTION

Systems and methods for motion evaluation in accordance with embodiments of the invention are illustrated. One embodiment includes a method for evaluating motion from a video. The method includes steps for identifying a set of one or more keypoint trajectories from a plurality of frames of a video, predicting a motion evaluation score based on the extracted set of keypoint trajectories, and providing an output based on the motion evaluation score.

In a further embodiment, identifying the set of keypoint trajectories includes identifying a set of keypoints within each of a plurality of frames of the video, and computing each keypoint trajectory of the set of keypoint trajectories based on positions of the keypoint in each frame of the plurality of frames.

In still another embodiment, the set of keypoints includes two-dimensional (2D) positions of joints and body keypoints of an individual captured in the video.

In a still further embodiment, identifying the set of keypoints includes using an OpenPose process to identify the set of keypoints.

In yet another embodiment, identifying the set of keypoint trajectories further includes computing additional features from the identified set of keypoints.

In a yet further embodiment, predicting the motion evaluation score includes providing the set of keypoint trajectories as inputs to a convolutional neural network (CNN), and computing the motion evaluation score based on outputs of the CNN.

In another additional embodiment, the motion evaluation score is one of gait deviation index (GDI), walking speed, cadence, symmetry, gait variability, and stride length.

In a further additional embodiment, providing the output includes providing a treatment regimen for a patient, based on the motion evaluation score.

In another embodiment again, providing the output includes providing a diagnosis for a disease. This can include the current state of a disease, the rate of progression of a disease, and a future state of a disease.

In a further embodiment again, the disease is one of Parkinson's disease, osteoarthritis, stroke, cerebral palsy, multiple sclerosis, and muscular dystrophy.

In still yet another embodiment, providing the output includes providing the output for an individual's progression based on a plurality of predicted motion evaluation scores over a period of time.

In a still yet further embodiment, providing the output includes providing real-time feedback to a user to adjust the user's motions.

In certain embodiments, providing the feedback includes providing real-time advice on how to reduce the risk of an injury. This includes advice on reduction of joint loads or muscle use.

In other embodiments, providing the output includes providing performance and injury risk metrics of professionals involved in physical work. This includes performance and injury risk metrics of athletes on an athletic field, or workers in a factory.

In still another additional embodiment, the method further includes performing a physics-based simulation based on the set of keypoint trajectories, and training a model based on the physics-based simulation, wherein predicting the motion evaluation score includes using the trained model to predict the motion evaluation score, wherein the motion evaluation score includes at least one of muscle activation, muscle fiber length, and joint loads.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Turning now to the drawings, systems and methods for evaluation of motion are disclosed. Systems and methods in accordance with many embodiments of the invention include a motion evaluation system that trains a model to evaluate motion (such as, but not limited to, gait) through images (or video) captured by a single image capture device. In certain embodiments, motion evaluation includes extracting clinically relevant variables from videos of patients walking.

Figure 1:
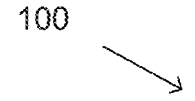
FIG. 1 illustrates a process for evaluating gait in accordance with an embodiment of the invention.
Figure 1:
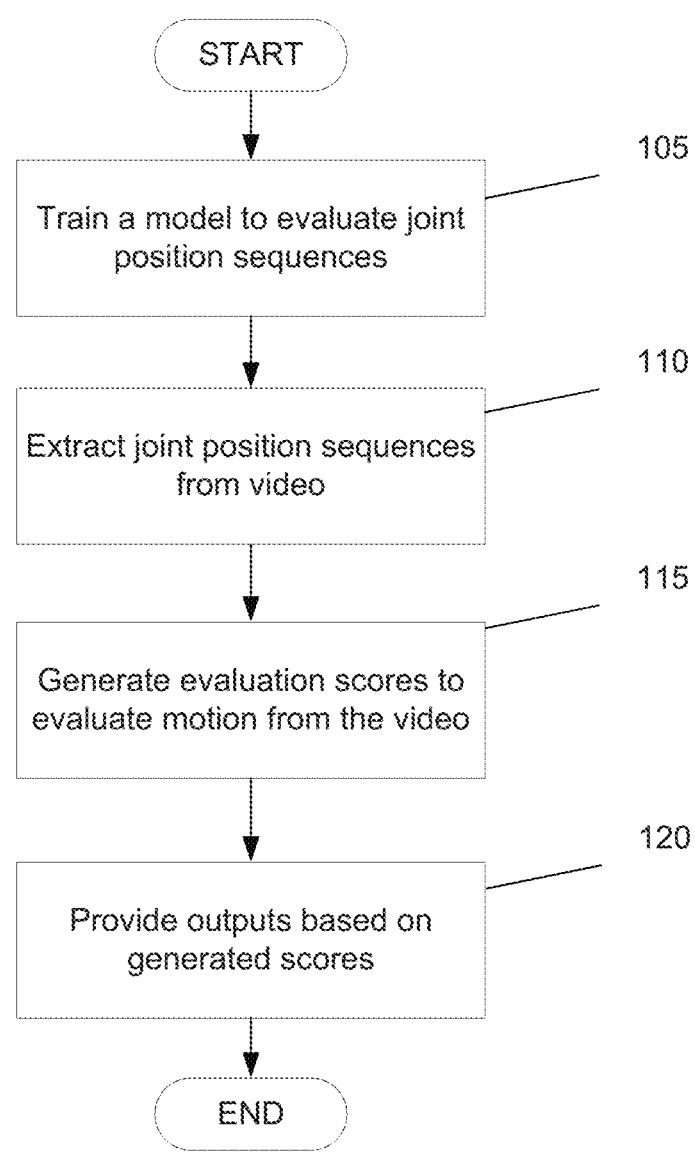

A process for evaluating gait in accordance with an embodiment of the invention is illustrated in FIG. 1. Process 100 trains (105) a model to evaluate keypoint trajectories identified from images (e.g., frames of a video). Keypoint trajectories in accordance with many embodiments of the invention are trajectories of 2D coordinates (or various other locators) of a number of body parts (or keypoints) (e.g., nose, hip, knees, ankles, toes, etc.) that are identified from the sequence of images. In a number of embodiments, in addition to based on the keypoints themselves, keypoint trajectories can also be evaluated based on features that are derived from keypoints, such as (but not limited to) estimated knee angles.

Figure 2:
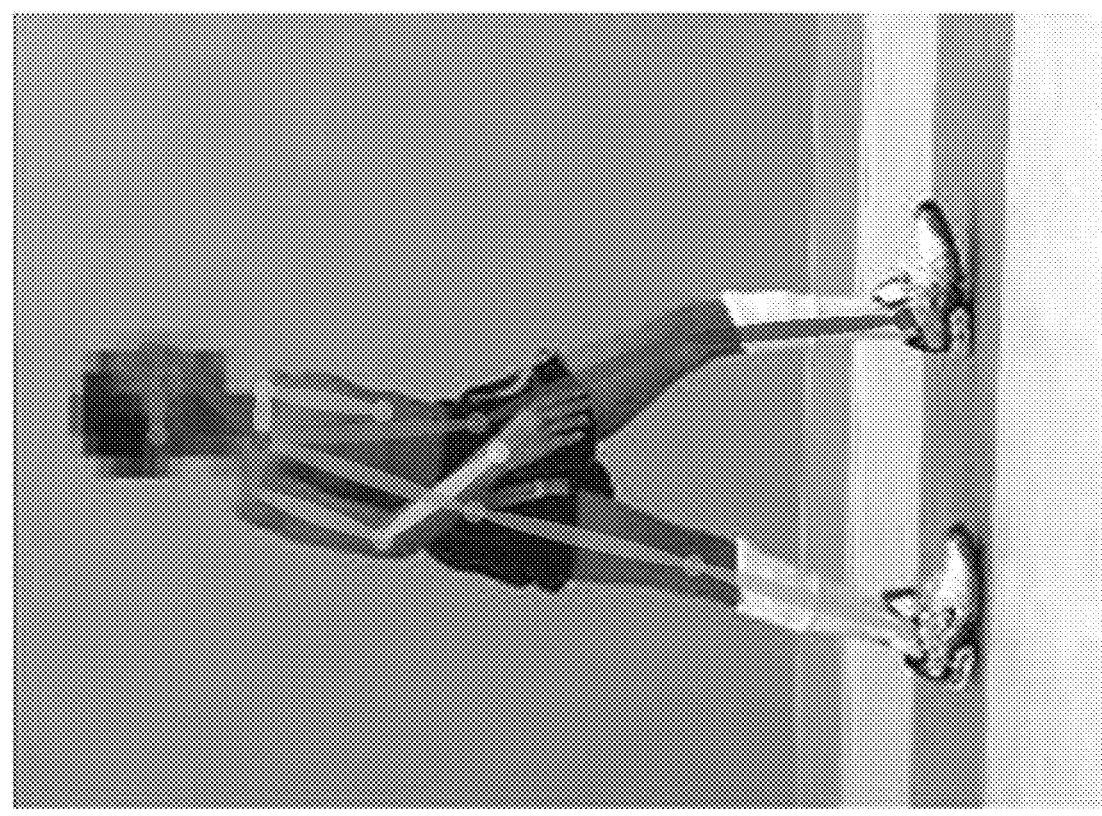
FIG. 2 illustrates examples of keypoints identified in an image.

Examples of keypoints identified in an image are illustrated in FIG. 2. In this example, keypoints are identified in an image, where each keypoint has (x, y) coordinates within the image. Keypoints in accordance with several embodiments of the invention include parts of the body that are visible in images of the body, and can be tracked through a sequence of images. In certain embodiments keypoints can include body parts such as (but not limited to) nose, ears, fingertips, and joints such as (but not limited to) knees, elbows. In certain embodiments, keypoints can be defined and/or annotated by a skilled professional (e.g., physiologist, biomechanist, etc.) in images of an individual. In several embodiments, keypoints can be identified with an image/video analysis library such as (but not limited to) OpenPose. Keypoints in accordance with many embodiments of the invention can also include body landmarks that are not directly visible, but which can be estimated from images of a person. Such keypoints can include (but are not limited to) elements of bones, muscles, joints, organs, and derivatives, such as (but not limited to) lateral compartment of a knee, middle of a femur. Multiple keypoints can be associated with each body part, such as (but not limited to) ten equidistributed keypoints along a tibia. One skilled in the art will recognize that a different number of keypoints and/or keypoints at different body parts can be used without departing from the spirit of the invention. In some embodiments, models are trained using keypoint trajectories as inputs to the model and an evaluation score as an output of the model. Models in accordance with a number of embodiments of the invention are trained using a set of video data that has been labeled with evaluation scores.

Process 100 extracts (110) keypoint trajectories identified from images of an individual performing a set of motions. In many embodiments, keypoint trajectories are extracted using the same or similar processes as those used to identify the keypoint trajectories from the training images. The extracted keypoint trajectories are used to evaluate the individual's ability to perform the set of motions. Sets of motions can include (but are not limited to) walking, running, dancing, and performing various exercises.

In certain embodiments, keypoint trajectories can be predicted using a machine learning model that is trained to predict "true" keypoint trajectories based on keypoint trajectories identified directly from the video. Machine learning models in accordance with numerous embodiments of the invention can be trained using video and corresponding motion capture data collected with the video, where the motion capture data is used as ground truth for the predicted keypoint trajectories.

Process 100 feeds the extracted keypoints trajectories to the trained model to generate (115) evaluation scores to evaluate the motion in the video. While there is a large body of research on mimicking marker-based motion capture using single- or multiple-cameras system, they often focus on reconstructing the 3D model. Systems in accordance with a number of embodiments of the invention provide an end-to-end system that directly outputs clinically-relevant variables, which can increase the accuracy and reduce the variability of outputs from the system. Evaluation scores in accordance with several embodiments of the invention include, but are not limited to, a gait deviation index (GDI), stride lengths, $O_2$ expenditure, maximum hip flexion, step width, muscle activity, muscle fiber length, joint loads, and other motion evaluation scores. GDI is a commonly adopted measure of gait abnormality, quantifying deviation of kinematic curves from kinematics of a typically developing child. GDI is a non-negative real number with smaller values indicating greater gait abnormality and values above 100 suggesting the absence of gait pathology. Traditionally, the GDI has been measured by collecting data from motion capture systems involving wearable sensors typically only available in a clinic. Processes in accordance with a number of embodiments of the invention allow for cost-effective, consistent, predictable, and convenient scoring of an individual's motion. Processes in accordance with a variety of embodiments of the invention can be used to recommend and/or predict the likelihood of future treatments including (but not limited to) surgery, physical therapy, and/or medication.

Process 100 provides (120) outputs based on the generated scores. In some embodiments, the evaluated motion is gait and providing output includes providing a treatment that involves one or more of providing therapeutic exercises to be performed by a patient (or user). In some embodiments, the generated evaluation scores are used by a physician to measure progress and to develop a treatment plan for a patient. In a number of embodiments, the individual is an athlete, the evaluated motion is a sports activity, and the treatment involves providing guidance in improving the athlete's performance in the evaluated motion. In many embodiments, the entire process can be performed at a user's device, allowing the user to capture and evaluate their motions based on the provided outputs. In certain embodiments, capture and outputs are performed at the user's device, but the analysis and score generations are performed in the cloud or at a set of one or more servers. In a number of embodiments, outputs can include various types of real-time feedback that can allow a user to adjust their motions based on their motion evaluation scores. Outputs in accordance with some embodiments of the invention can include historical progression data that tracks the progress of a user over a period of time.

Systems for Clinical Gait Evaluation

Motion Evaluation System

Figure 3:
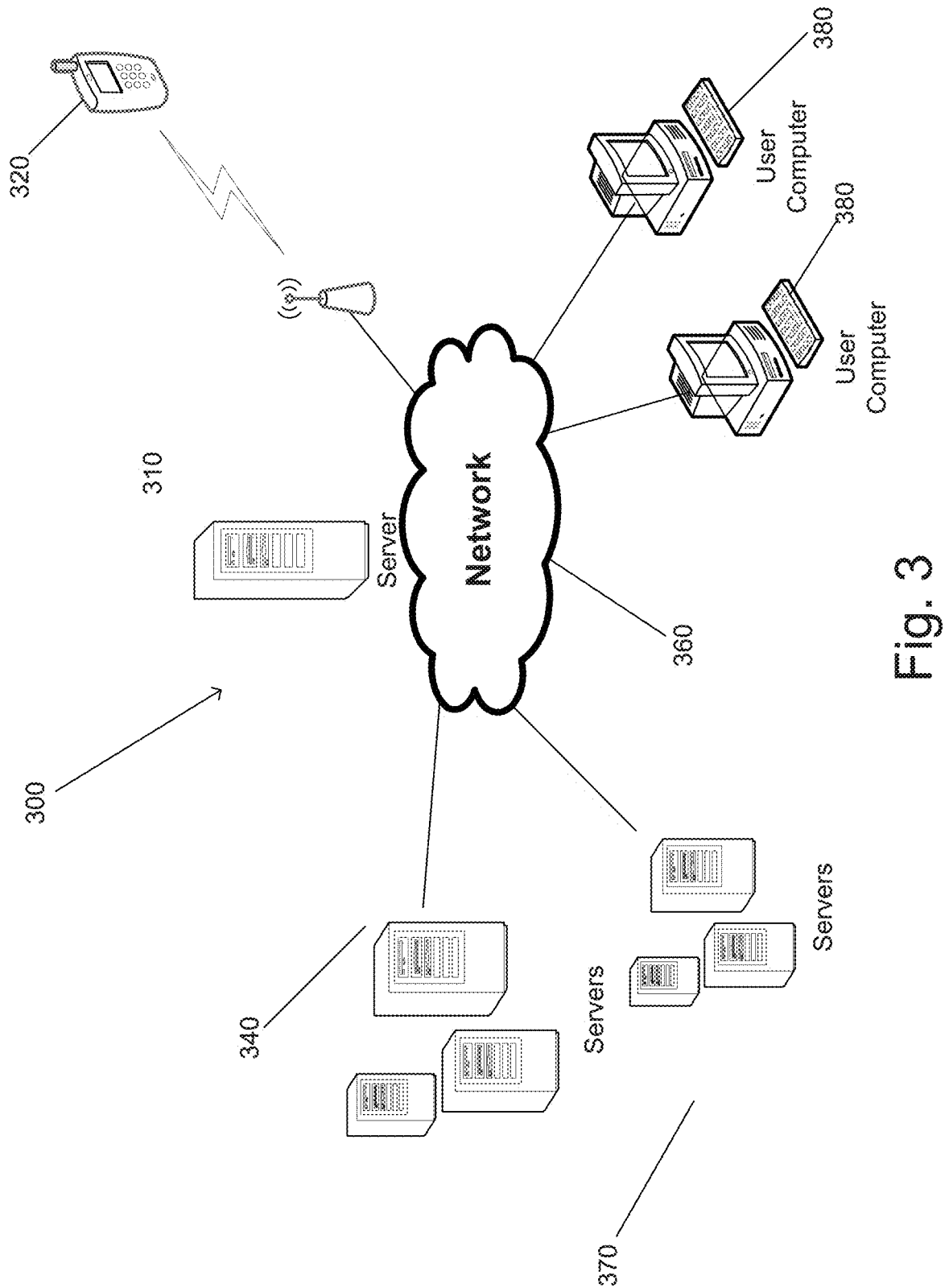
FIG. 3 illustrates a system for evaluating motion from a video in accordance with some embodiments of the invention.

A system for evaluating motion from a video in accordance with some embodiments of the invention is illustrated in FIG. 3. Network 300 includes a communications network 360. The communications network 360 is a network such as the Internet that allows devices connected to the network 360 to communicate with other connected devices. Server systems 310, 340, and 370 are connected to the network 160. Each of the server systems 310, 340, and 370 is a group of one or more servers communicatively connected to one another via networks that execute processes that provide cloud services to users over the network 360. For purposes of this discussion, cloud services are one or more applications that are executed by one or more server systems to provide data and/or executable applications to devices over a network. The server systems 310, 340, and 370 are shown each having three servers in the internal network. However, the server systems 310, 340 and 370 may include any number of servers and any additional number of server systems may be connected to the network 360 to provide cloud services. In accordance with various embodiments of this invention, motion evaluation can be provided by executing one or more processes on a single server system and/or a group of server systems communicating over network 360.

Users may use personal devices 380 and 320 that connect to the network 360 to perform processes for capturing images (or video) of a user and/or analyzing motion based on the captured images with various embodiments of the invention. In the illustrated embodiment, the personal devices 380 are shown as desktop computers that are connected via a conventional "wired" connection to the network 360. However, the personal device 380 may be a desktop computer, a laptop computer, a smart television, an entertainment gaming console, or any other device that connects to the network 360 via a "wired" and/or "wireless" connection. Personal devices in accordance with many embodiments of the invention include an image capture device (e.g., webcam, camera, etc.) for recording images of a user performing a set of motions. Image capture devices in accordance with certain embodiments of the invention include a set of one or more image capture devices that can be used to capture video data of a user in motion. Given a single-camera or a multi-camera data collection setting, systems in accordance with a number of embodiments of the invention can use artificial neural networks (such as, but not limited to, convolutional neural networks, recurrent neural networks, etc.) for extracting trajectories of keypoints from sequences of images. In many embodiments, trajectories of keypoints can be used to train a separate statistical model (such as, but not limited to, CNNs, SVRs, RRs) for predicting a set of motion parameters, such as (but not limited to) Gait Deviation Index (GDI), Gross Motor Function Classification System (GMFCS), stride length, and gait asymmetry.

The mobile device 320 connects to network 360 using a wireless connection. A wireless connection is a connection that uses Radio Frequency (RF) signals, Infrared signals, or any other form of wireless signaling to connect to the network 160. In FIG. 3, the mobile device 320 is a mobile telephone. However, mobile device 320 may be a mobile phone, Personal Digital Assistant (PDA), a tablet, a smartphone, or any other type of device that connects to network 360 via a wireless connection without departing from this invention. In many embodiments, an application being executed by the user device may capture or obtain images of a user's motion and transmit the captured images to a server system that performs additional processing (such as, but not limited to, clinical evaluations) based upon the received images. Although references are made to images throughout this application, one skilled in the art will recognize that processes described in this application can clearly be applied to video (or video frames) without departing from this invention. In accordance with many embodiments of the invention, processes for capturing images (or video) of an individual and/or evaluating motion based on the captured images can be performed by various motion evaluation elements of the system, either individually, or in a distributed fashion across multiple devices (e.g., servers, personal devices, etc.). Systems in accordance with many embodiments of the invention can allow a user to perform gait checkups at home, using a camera or a mobile device, which can allow for early detection for signs of neurological disorders or the tracking of progress between visits for a patient's physical therapy, which can also be shared across a network with a physician or other medical professional.

Motion Evaluation Element

Figure 4:
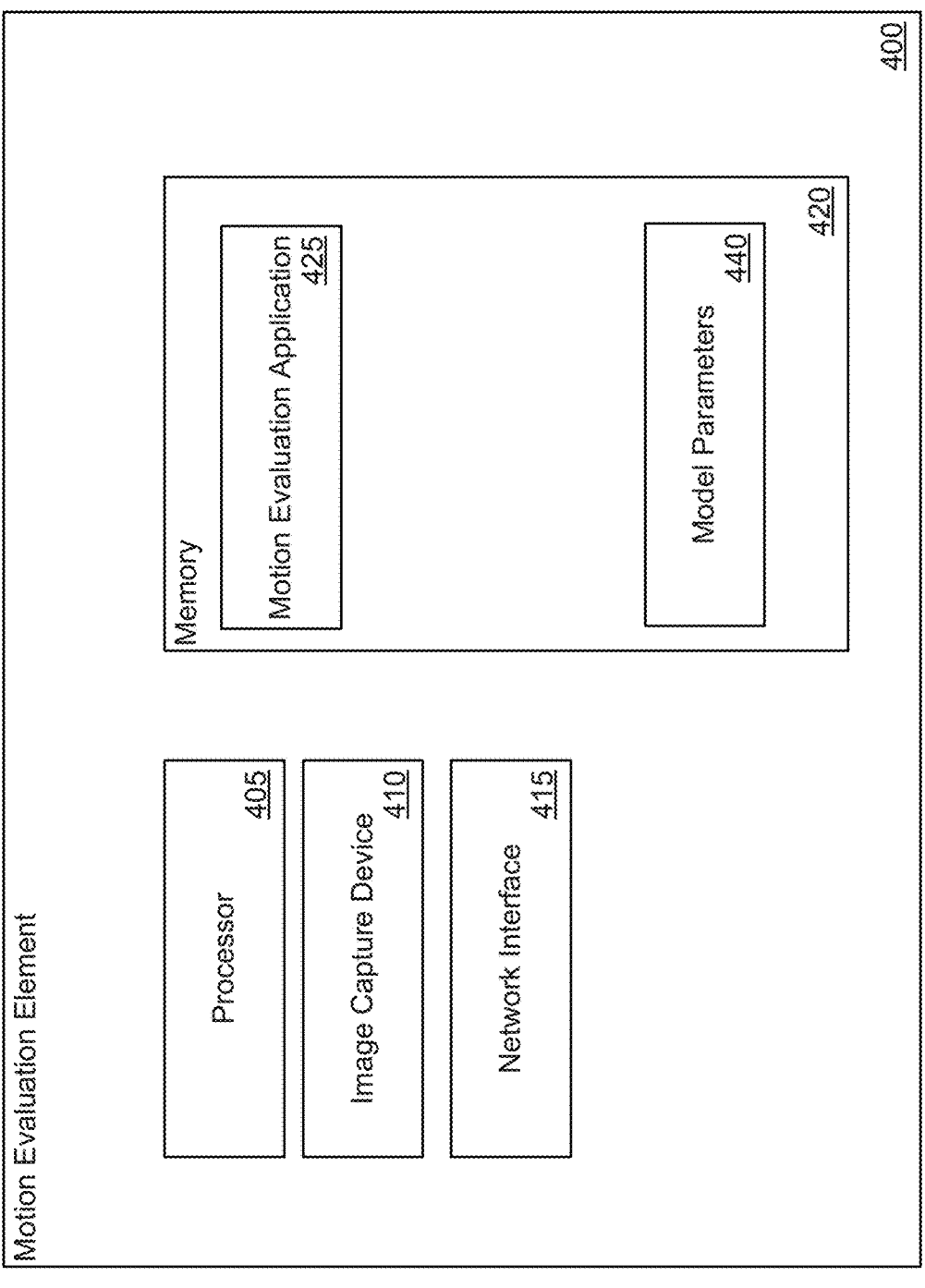
FIG. 4 illustrates a motion evaluation element in accordance with an embodiment of the invention.

An example of a motion evaluation element in accordance with an embodiment of the invention is illustrated in FIG. 4. In some embodiments, motion evaluation elements can enable data collection in clinics that that are not equipped with the expensive motion capture systems that are often required in current processes. Motion evaluation elements in accordance with several embodiments of the invention allow for accurate, consistent, and clinically relevant output with low-cost systems, such as (but not limited to) mobile phones and/or personal computers. In several embodiments, systems allow for the early detection of signs of neurological disorders and can allow for the collection vast amounts of clinically relevant motion data at scale.

Motion evaluation element 400 includes a processor 405, image capture device 410, network interface 415, and memory 420. One skilled in the art will recognize that a particular motion evaluation element may include other components that are omitted for brevity without departing from this invention. The processor 405 can include (but is not limited to) a processor, microprocessor, controller, or a combination of processors, microprocessor, and/or controllers that performs instructions stored in the memory 420 to manipulate data stored in the memory. Processor instructions can configure the processor 405 to perform processes in accordance with certain embodiments of the invention. Image capture device 415 can capture and/or retrieve images for the motion evaluation element. Image capture devices can include (but are not limited to) cameras and other sensors that can capture image data of a scene. Network interface 415 allows motion evaluation element 400 to transmit and receive data over a network based upon the instructions performed by processor 405.

Memory 420 includes a motion evaluation application 425 and model parameters 440. Motion evaluation applications in accordance with several embodiments of the invention are used to evaluate motion of a subject based on a model trained using model parameters and/or weights to generate scores for evaluating the motion.

Although a specific example of a motion evaluation element 400 is illustrated in FIG. 4, any of a variety of motion evaluation elements can be utilized to perform processes similar to those described herein as appropriate to the requirements of specific applications in accordance with embodiments of the invention.

Motion Evaluation Application

Figure 5:
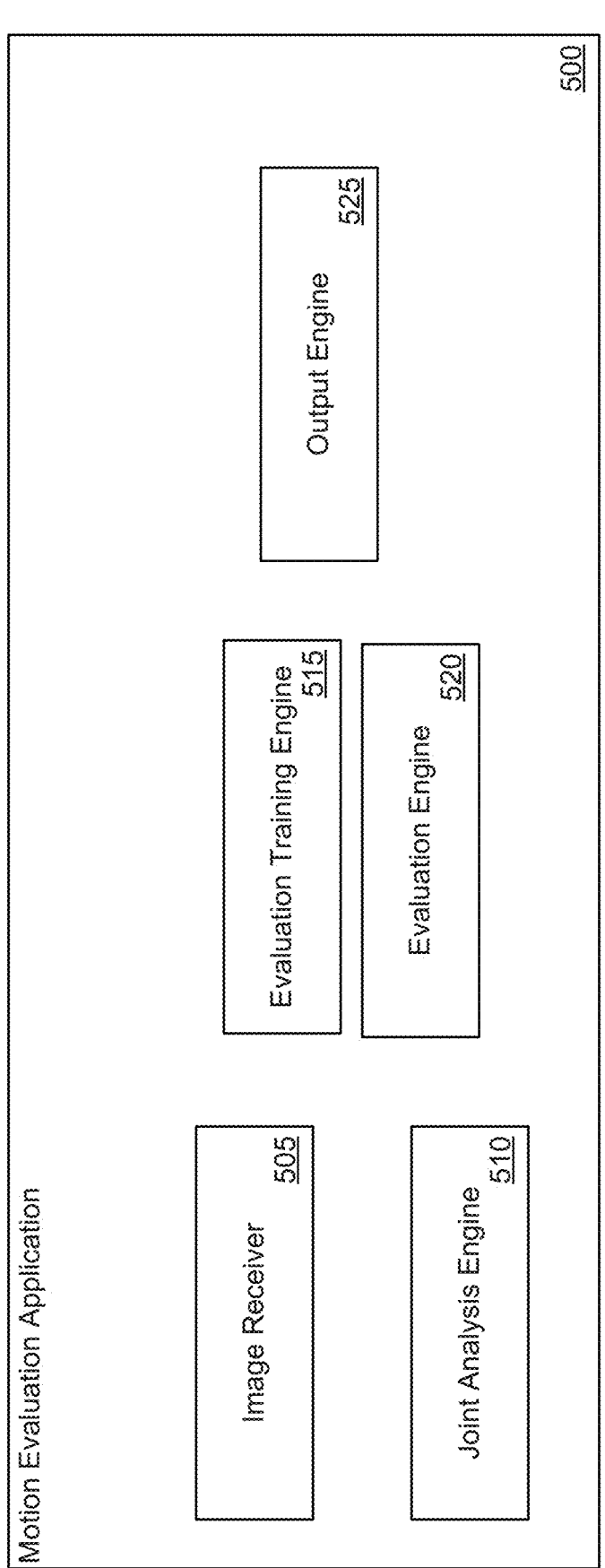
FIG. 5 illustrates a motion evaluation application in accordance with a number of embodiments of the invention.

A motion evaluation application in accordance with a number of embodiments of the invention is illustrated in FIG. 5. Motion evaluation application 500 includes image receiver 505, joint analysis engine 510, evaluation training engine 515, evaluation engine 520, and output engine 525. In many embodiments, motion evaluation applications operate on mobile devices, improving accessibility, reducing costs, and allowing a user to quickly and efficiently evaluate motion of an individual.

Image receivers in accordance with many embodiments of the invention are for receiving or capturing images and/or videos of an individual as they perform a set of motions. Joint analysis engines in accordance with several embodiments of the invention can be used to analyze the images of an individual to identify the positions of an individual's joints and their movements over a sequence of images or frames of a video. In some embodiments, videos recorded by cameras are processed in the pipeline using artificial neural networks. For example, in some embodiments a keypoint estimation library (such as, but not limited to) OpenPose is used for real-time keypoint detection from video images.

In some embodiments, evaluation training engines can be used to train a model to evaluate motion based on keypoint trajectories. Evaluation training engines in accordance with several embodiments of the invention can train the evaluation engines (or models) to directly output a clinically relevant variable, such as (but not limited to) Gait Deviation Index (GDI) or to provide other types of scores for various different motions. Evaluation training engines in accordance with many embodiments of the invention can train a CNN to generate motion evaluation scores based on 2-D coordinates for the keypoints of the keypoint trajectories.

In some embodiments, labels (e.g., parameter values) for training evaluation engines can be derived from physics simulations of human motion. In many embodiments, a physical model can be fed data from a motion capture trial in order to approximate physical parameters (such as, but not limited to, muscle activation, muscle fiber length, and joint loads) using a physics library such as, but not limited to, OpenSim. Training in accordance with some such embodiments can allow a trained evaluation engine to directly predict such physical parameters from new motion capture data.

Evaluation engines in accordance with a number of embodiments include one or more statistical models, such as (but not limited to) CNNs, SVRs, and RRs. In many embodiments, evaluation engines are trained using evaluation training engines to generate scores for captured motion videos without translating motions to 3-D or calculating other joint and/or motion parameters, such as stride length, ankle angles, knee angles, etc. Examples of some evaluation engines are described in further detail below.

Output engines in accordance with several embodiments of the invention can provide a variety of outputs to a user, including (but not limited to) treatment interventions for correcting anomalies in a user's motion, physical therapy exercises, as well as displaying, recording, and/or transmitting scores for tracking progress of the individual. In a number of embodiments, outputs can include various types of real-time feedback that can allow a user to adjust their motions based on their motion evaluation scores. Feedback in accordance with a number of embodiments of the invention can include (but is not limited to) real-time advice on how to reduce the risk of an injury and/or advice on reduction of joint loads and/or or muscle use. In a number of embodiments, outputs can include performance and/or injury risk metrics (e.g., for professionals involved in physical work, athletes during a training session, etc.). Outputs in accordance with some embodiments of the invention can include historical progression data that tracks the progress of a user over a period of time.

Evaluation Engines

Evaluation engines in accordance with many embodiments of the invention can be used to evaluate a timed trajectory of keypoints in images of an individual to provide a quantitative score for the individual's motions. In some embodiments, evaluation engines can include one or more models, such as (but not limited to) convolutional neural networks, support vector regression, ridge regression, and random forests.

Support Vector Regression

Support vector regression (SVR) seeks to learn a set of weights w, b that solve the following optimization problem:

$$\text{minimize } \frac{1}{2}\|w\|^2 + C\sum_{i=1}^{\ell}(\xi_i + \xi_i^*)$$

$$\text{subject to } \begin{cases} y_i - \langle w, x_i \rangle - b \leq \epsilon + \xi_i \\ \langle w, x_i \rangle + b - y_i \leq \epsilon + \xi_i^* \\ \xi_i \xi_i^* \geq 0 \end{cases}$$

The predicted value for a given x is then $\langle w, x \rangle + b$. The idea here is that only points outside a specified tolerance E are penalized (according to a parameter C). Just like with support vector machines, it is possible to apply a kernel trick to work in a higher dimensional feature space. In some embodiments, a gridsearch is conducted to tune C and $\in$ for the SVR.

In some embodiments, the radial basis function can be used as the kernel for the SVR.

Ridge Regression

Ridge regression is an example of penalized regression that combines $\ell_2$ regularization with ordinary least squares. It seeks to find weights β that minimize the cost function:

$$\sum_{i=1}^{m} (y_i - x_{iT}\beta)^2 + \alpha \sum_{j=1}^{p} \beta_j^2$$

One benefit of ridge regression is that it allows a trade-off between variance and bias: lower values of a correspond to less regularization, hence greater variance and less bias. The reverse is true for higher values of a. In some embodiments, gridsearch is conducted to tune a for the RR.

Convolutional Neural Networks (CNNs)

Neural networks work well in evaluating motion because they are able to come up with useful features from a raw time series, without extensive manual feature engineering required in other processes. Convolutional Neural Networks (CNNs) are a type of neural network that use the ideas of parameter sharing and sparse connectivity to constrain the model architecture and reduce the number of parameters that need to be learned. The distinguishing characteristic of a CNN is the presence of convolutional layers, which are often combined with max pooling layers. In some embodiments, CNNs implement 1-D and/or 2-D convolutional layers. In many embodiments, the input to a 1-D convolutional layer consists of a T×D set of neurons, where T is the number of points in the time dimension and D is the depth, or the dimension of the multivariate time series input into the model. In a number of embodiments, each 1-D convolutional layer learns the weights of a set of filters of a given length. For instance, suppose a convolutional layer learns filters of length F. Each filter can connect only the neurons in a local region of time (but extending through the entire depth) to a given neuron in the output layer. Thus, each filter consists of FD+1 weights (including a bias term), so the total number of parameters to an output layer of depth D2 is (FD+1)D2.

Figure 6:
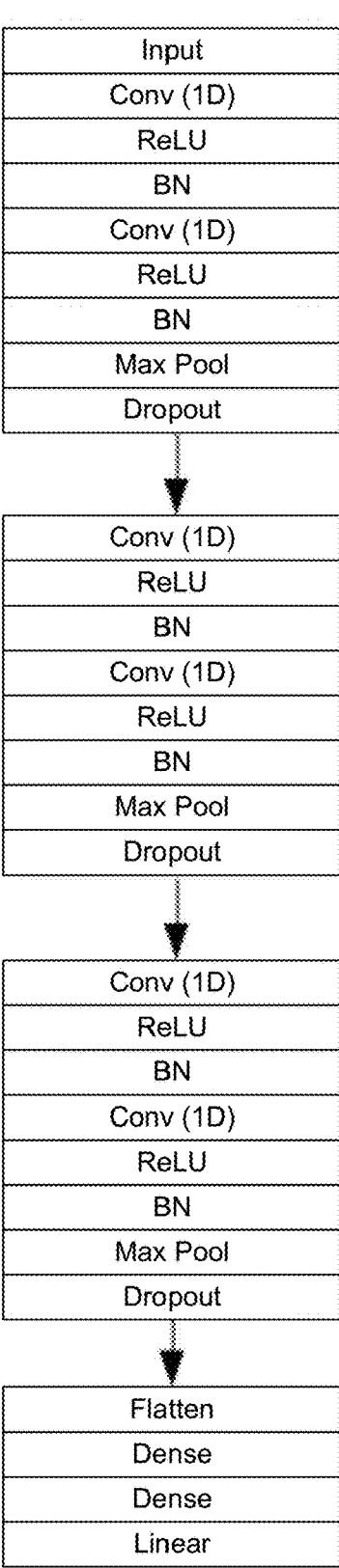
FIG. 6 illustrates an example of a CNN architecture in accordance with an embodiment of the invention.

An example of a CNN architecture in accordance with a number of embodiments of the invention is illustrated in FIG. 6. The illustrated architecture shows a CNN with 6 1-D convolutional layers. Convolutional layers in accordance with a number of embodiments include 32 filters and a filter length of 8.

Activation functions are applied after each convolutional layer. In this example, a rectified linear unit (ReLU) is used as the activation function, but activation functions in accordance with several embodiments of the invention can include (but are not limited to) ReLU, sigmoid functions, and tan h functions. CNN architectures in accordance with several embodiments of the invention can apply batch normalization (BN) before or after the activation functions. Additionally, in many embodiments, a max pooling layer is added after every two convolutional layers and dropout (e.g., with rate 0.5) is applied. In many embodiments, mini batches are used with RMSProp as the optimizer. RMSProp is described in further detail in the presentation available at www.cs.toronto.edu/-tijmen/csc321/slides/ lecture_slides_lec6.pdf, the disclosure of which is incorporated by reference herein in its entirety.

In some embodiments, coordinates are filtered, or dropped, from the input data, as certain time series can be too noisy to be helpful based on the motion being evaluated. For example, the x-coordinate of the left ear may not provide meaningful input when evaluating a person's gait. Dropping noisy position coordinates from the input data for training the model and for generating the motion evaluations can provide more accurate results and improved computing performance.

In certain embodiments, systems and methods perform a random search on a small grid to tune the initial learning rate of RMSProp and the learning rate decay schedule. Training the model in accordance with many embodiments of the invention includes various steps for optimizing the training of the model, including (but no limited to) searching over different values of L2 regularization to apply to later convolutional layers, decaying the learning rate, and applying early stopping to iterations of the random search that had problems converging.

Based on experimental results, CNN models achieve improved (correlation/accuracy) in comparisons with other models. In some embodiments, evaluation engines can ensemble a few different CNN models (or other types of models) together to improve performance.

Figure 7:
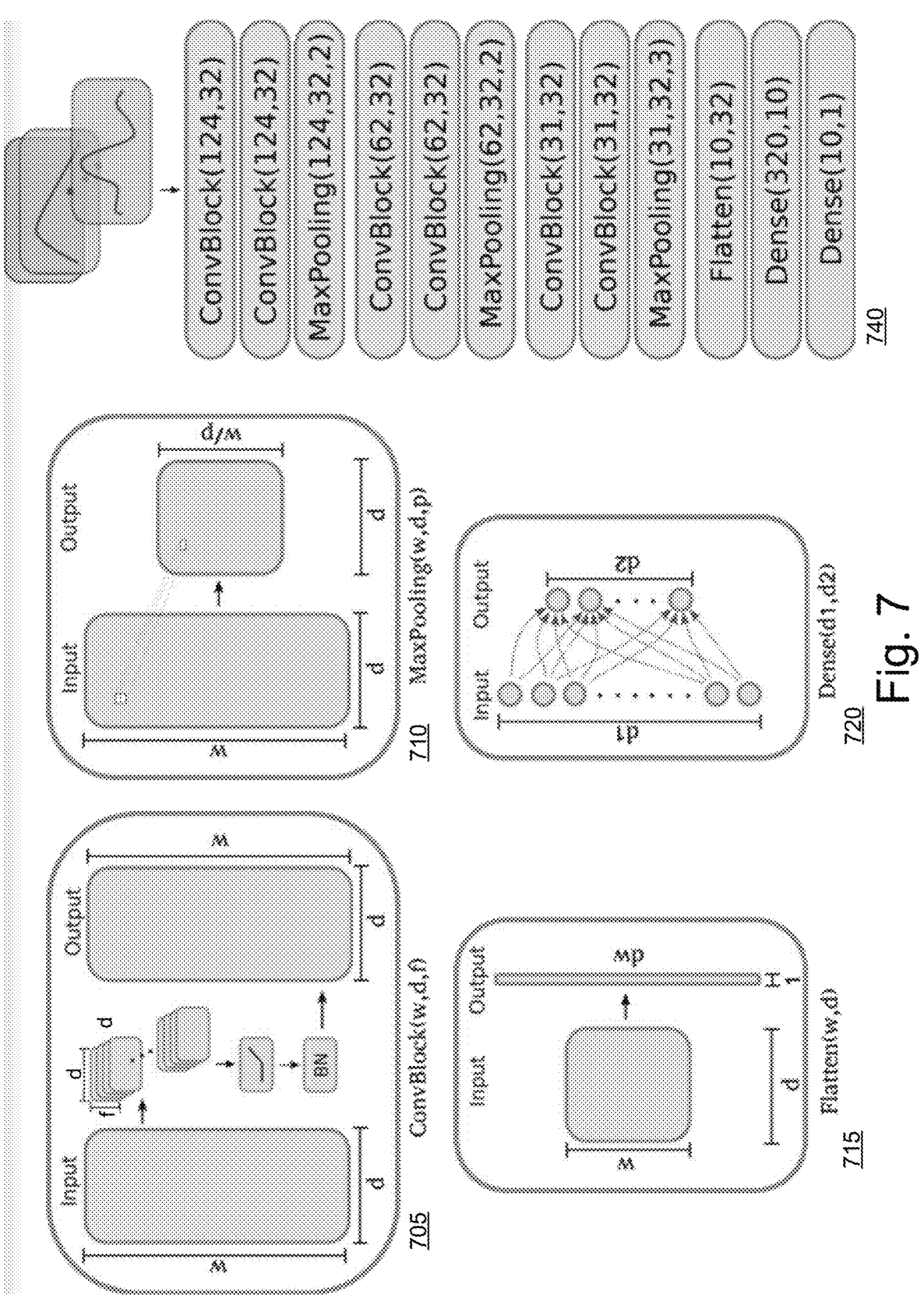
FIG. 7 illustrates another example of a CNN architecture in accordance with an embodiment of the invention.

Another example of a CNN in accordance with some embodiments of the invention is illustrated in FIG. 7. In this example, the CNN is composed of four types of blocks. Convolutional block (ConvBlock 705) maps a multivariate time series into another multivariate time series using parameterized one-dimensional convolutions. Maximum pooling block (MaxPooling 710) extracts maximum value from a sequence of p values, thus reducing the dimensionality by a factor of p. Flattening block (Flatten 715) changes the shape of an array to a vector. Dense block (Dense 720) is a multiple linear regression with a nonlinear function at the output. Diagram 740 shows a sequential combination of these blocks used in models in accordance with several embodiments of the invention.

Training for Clinical Gait Evaluation

Figure 8:
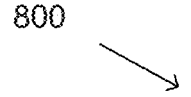
FIG. 8 conceptually illustrates a process for training a model for clinical gait evaluation.
Figure 8:
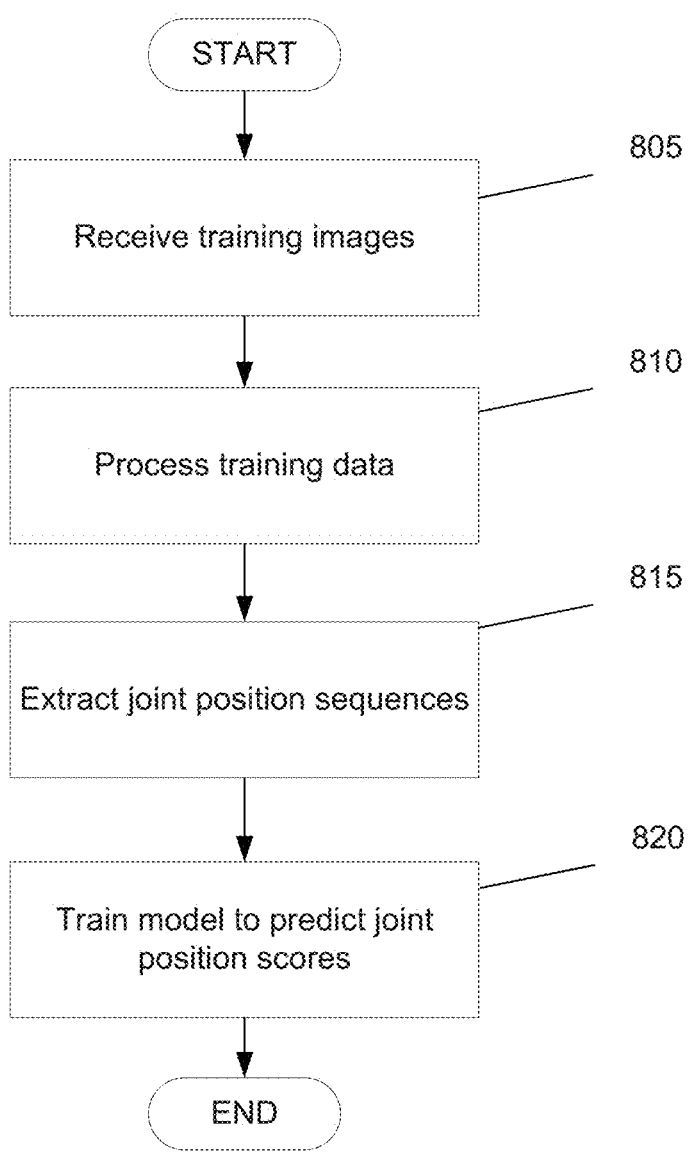

A process for training a model for clinical gait evaluation is conceptually illustrated in FIG. 8. Process 800 receives (805) input images (or video). In many embodiments, received inputs include (but are not limited to) videos of a user walking and/or otherwise performing a set of motions. Processes in accordance with some embodiments of the invention can use images from a single video captured from a single perspective. In some embodiments, processes can receive input images from multiple different videos captured from multiple different perspectives. Processes in accordance with some embodiments of the invention can use images from multiple videos captured at different times to evaluate an individual's disease progression. In many cases, the use of multiple perspectives can allow for more accurate scoring an individual's gait.

In some embodiments, the input comprises videos of patients walking, which have been evaluated and annotated by medical professionals. Annotations can include (but are not limited to) GDI, GMFCS, descriptive text, and/or measured evaluations (e.g., stride length, etc.). In some embodiments, the received inputs are pre-processed to normalize the inputs for analysis. For example, videos in accordance with some embodiments of the invention are converted to a resolution of 640×480 and 25 frames per second.

Process 800 processes (810) the training data with additional data. In some embodiments, the training data is not processed before being used to train an evaluation engine. However, in many embodiments, the training data is processed to improve the ability of the model to learn. In certain embodiments, processing the data includes augmenting the data to increase the accuracy and improve the models ability to generalize for various factors, including (but not limited to) different perspectives, camera settings, camera jitter, and lighting conditions. In many cases, labeled data for motion evaluation is not available at scale. In some embodiments, the existing data is divided into multiple samples, allowing the model to train on different portions of the video to evaluate the motion based on the different portions of the video.

Processes in accordance with many embodiments of the invention process the training data by filtering extracted keypoint trajectories to remove time series in which a threshold amount (e.g., 50%) of the data is missing. In some embodiments, extraneous frames are removed so that the extracted trajectories only include captures of motions relevant to a particular application.

In some embodiments, processing the training data includes generating features of a user's motion, such as (but not limited to) step length, cadence, and peak knee flexion. In some embodiments, different features are generated for different evaluation engines. For example, processes in accordance with a number of embodiments of the invention engineer summary statistics of the raw and derived time series for the SVR and RR models, such as (but not limited to) the mean, variance, 10th percentile, and 90th percentile.

In some embodiments, processing the training data includes deriving time series that can be helpful for improving the performance of the CNN. Derived time series in accordance with certain embodiments of the invention can include a time series that is simply the difference between the x-coordinate of the left ankle and the x-coordinate of the right ankle throughout time. In some embodiments, derived time series include an approximation the angle formed by the left ankle, left knee, and left hip. In numerous embodiments, time series can be derived separate for opposite sides (e.g., right and left sides) of the body. To elaborate, let $v_1 \in R^2$ be the vector resulting from subtracting the coordinates of the left ankle from the left knee, and $v_3 \in R^2$ be the vector resulting from subtracting the coordinates of the left knee from the left hip. The approximated angle feature is then $$\arccos\left(\frac{(v_1 v_2)}{\|v_1\| * \|v_2\|}\right)s.$$

Note that this is only an approximation of the angle because the z coordinates of these keypoints is not known.

In a number of embodiments, each bivariate time series of (x,y) coordinates of a keypoint over time can be centered (e.g., by subtracting the coordinates of the right hip) and scaled (e.g., by dividing it by the Euclidean distance between the right hip and the right shoulder). The univariate time series of each coordinate can then be smoothed (e.g., using a one-dimensional Gaussian filter) and missing values can be imputed (e.g., using linear interpolation). A time series can be defined as a discrete sequence $X_t \in R^d$ for $t \in (1, \ldots, T)$ and $T \in N$. A time series is a univariate time series if $d=1$, a bivariate time series if $d=2$, and a multivariate time series if $d>1$.

In many embodiments, processing the training data includes methods for augmenting the training data. Time series data in accordance with many embodiments of the invention is augmented using window slicing. From each input time series X with a given length L in the time dimension and an associated evaluation score y, overlapping segments can be extracted. In some embodiments, each overlapping segment has a same length. For instance, given a data point (y;X) of length 500, overlapping segments (y;X[:,0: 124]), (y,X[:, 31: 155]), . . . (y,X[:; 372: 496]) can be identified, with each segment being of length 124, and overlapping with one or more of the neighboring segments. Each segment can be labelled with the same evaluation score as the video that contains it. In certain embodiments, all segments that have more than 50% of their data missing are dropped from the input data.

For a given video $X^{(i)}$, the notation $X_j^{(i)}$,j=1,2 . . . c(i) is used to refer to its derived segments, where c(i) counts the number of segments that are in the training set. Since some videos have more segments that end up in the training set than others (due to different amounts of missing data), the L2 loss function in accordance with a number of embodiments of the invention can be modified so that videos with more available segments are not overly emphasized during training. The modified loss function, $L(y_i, CNN(X_j^{(i)}))=(y_i-CNN(X_j^{(i)}))^2/c(i)$, calculates the loss for a segment $X_j^{(i)}$ by squaring the difference between the actual score for the video and the score predicted for the segment j, divided by the number of segments of the video. In this way, the loss for each video is the mean squared error of the segments of that video so that a video with many segments is not overly emphasized during training.

Once the training data is processed, process 800 extracts (715) trajectories of keypoints. Keypoint trajectories can be extracted using a number of methods including (but not limited to) OpenPose, CNNs, image processing algorithms, and/or manual annotations. In some embodiments, processes use the OpenPose algorithm to extract 2D body landmark positions (such as knees, ankles, nose, etc.) in each frame of the video. The OpenPose algorithm is described in greater detail in "Realtime Multi-Person 2D Pose Estimation using Part Affinity Fields," by Cao et al., the disclosure of which is incorporated herein in its entirety.

Processes in accordance with several embodiments of the invention can extract (815) multivariate time series from videos. In some embodiments, multivariate time series include 36-dimensional multivariate time series comprising the (x, y) coordinates of 18 different body parts (such as, but not limited to, noses, knees, hips, ankles, and/or toes).

Process 800 trains (820) a model to predict a quantitative motion evaluation score based on the extracted multivariate time series. In some embodiments, the model is trained based on labeled data, in which each video is annotated with a true motion evaluation score. The model is then trained to generate predictions that are similar to the scores assigned to the annotated videos. In many embodiments, no intermediate prediction of 3D positions or other intermediate parameters, such as (but not limited to) stride length, knee angles, etc. By avoiding the intermediate predictions and intermediate parameters, models trained in accordance with many embodiments of the invention can provide more accurate evaluation scores with fewer calculations.

In many embodiments, the predicted metric (e.g., GDI) of each of a given video's segments are averaged together to get the final predicted metric (or score) for the video. However, this averaging operation can introduce bias. In some embodiments, the bias can be estimated by fitting a linear model on the training set and using the fitted linear model to remove the bias of the validation set predictions.

Figure 9:
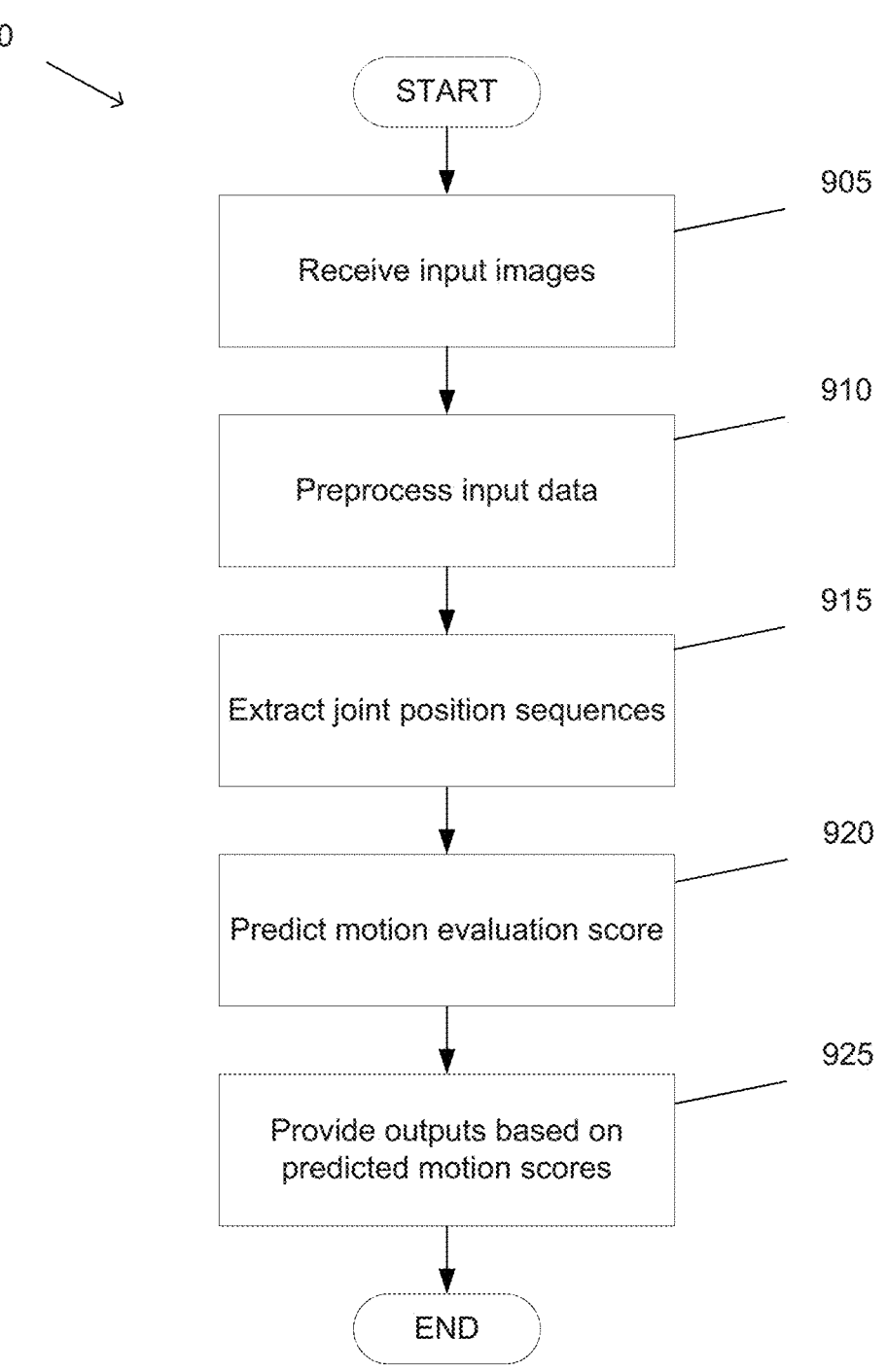
FIG. 9 conceptually illustrates a process for generating motion evaluation scores in accordance with an embodiment of the invention.

A process for generating motion evaluation scores in accordance with an embodiment of the invention is conceptually illustrated in FIG. 9. Process 900 receives (905) input images, preprocesses (910) the input images, extracts (915) keypoint trajectories, predicts (920) motion evaluation scores, and provides (925) output based on the predicted motion evaluation scores. In many embodiments, steps for receiving input images, preprocessing the input images, and extracting keypoint trajectories are similar to those described with reference to FIG. 7.

Once keypoints have been extracted from the input images, processes in accordance with many embodiments of the invention predict the motion evaluation scores using one or more evaluation engines (or models) to generate scores for the input images. In some embodiments, multiple scores can be calculated for each set of input images, and a composite score is calculated based on an aggregation of the individual scores. For example, in some embodiments, a video is divided into segments, a score is generated for each segment, and a composite score for the video is generated based on the individual segment scores.

In some embodiments, the predicted motion evaluation scores can be used as a part of a diagnostic tool for predicting or detecting the early onset of medical conditions such as cerebral palsy or Parkinson's disease. It is expected that, even if the predicted GDI is not perfectly correlated with the "true" GDI, it could theoretically be more predictive of such medical conditions because of the way that the evaluation engines are trained and the ability of such models to identify characteristics that may not be readily visible to a medical professional. In numerous embodiments, outputs from a process can include a diagnosis for a disease. Diagnoses in accordance with numerous embodiments of the invention can include (but are not limited to) the current state of a disease, the rate of progression of a disease, and a future state of a disease.

Processes in accordance with a number of embodiments of the invention provide outputs based on the predicted motion evaluation scores. In some embodiments, the evaluated motion is gait and providing output includes providing a treatment that involves one or more of providing therapeutic exercises to be performed by a patient. In some embodiments, the generated evaluation scores are used by a physician to measure progress and to develop a treatment plan for a patient. In a number of embodiments, the individual is an athlete, the evaluated motion is a sports activity, and the treatment involves providing guidance in improving the athlete's performance in the evaluated motion.

Applications of Motion Evaluation

Although many of the examples described above are described with reference to gait analysis, the collection of human motion data is a fundamental part of various commercial, scientific, and medical work flows. For example, motion capture is frequently performed in the movie and gaming industries, and biomechanics researchers commonly record motions of individuals as they walk or run across a motion capture laboratory. The evaluation of motions can also be used in a variety of other fields, including (but not limited to) self-driving cars, security monitoring, and many others.

For example, systems in accordance with many embodiments of the invention might readily be modified for different types of movement, such as analysis of the range of motion of arms or analysis of certain movement in sport (e.g. golf swing, basketball free throws, etc.). It can be used to support physical therapy (a user can get a score for each exercise, etc.).

Although specific methods of evaluation motion with a single camera are discussed above, many different evaluation methods can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A method for evaluating motion from a video, the method comprising:

identifying a set of one or more keypoint trajectories from each of a plurality of frames of a video;

providing the set of one or more keypoint trajectories as inputs to an artificial neural network, wherein the artificial neural network is trained using multivariate time series of coordinates of a set of one or more keypoint trajectories extracted from at least one training video, wherein each of the at least one training video is annotated with a true motion evaluation score, wherein the artificial neural network is trained to predict motion evaluation scores based on the multivariate time series of coordinates and the true motion evaluation score of the corresponding training video where the multivariate time series of coordinates are extracted from, wherein the artificial neural network comprises a convolutional neural network having one or more convolutional layers, wherein each of the one or more convolutional layers is configured to:

receive as input, a multivariate time series of coordinates structured as a T×D matrix, where T represents a number of points in a time dimension of the multivariate time series of coordinates, and D represents a depth dimension of the multivariate time series of coordinates; and apply one or more filters of a filter length F to the multivariate time series of coordinates, wherein each filter connects to a local region in the time dimension comprising F consecutive points in the time dimension, and wherein each filter extends through an entirety of the depth dimension such that each filter connects to all D features at each of the F consecutive points in the time dimension;

computing the motion evaluation score based on the set of one or more keypoint trajectories using the artificial neural network; and providing an output based on the motion evaluation score.

2. The method of claim 1, wherein identifying the set of keypoint trajectories comprises:

identifying a set of keypoints within each of a plurality of frames of the video;

computing each keypoint trajectory of the set of keypoint trajectories based on positions of the keypoint in each frame of the plurality of frames.

3. The method of claim 2, wherein the set of keypoints comprises two-dimensional (2D) positions of joints and body keypoints of an individual captured in the video.

4. The method of claim 3, wherein identifying the set of keypoints comprises using an OpenPose process to identify the set of keypoints.

5. The method of claim 1, wherein identifying the set of keypoint trajectories further comprises computing additional features from the identified set of keypoints.

6. The method of claim 1, wherein the motion evaluation score is one of gait deviation index (GDI), walking speed, cadence, symmetry, gait variability, and stride length.

7. The method of claim 1, wherein providing the output comprises providing a treatment regimen for a patient, based on the motion evaluation score.

8. The method of claim 1, wherein providing the output comprises providing a diagnosis for a disease.

9. The method of claim 8, wherein the disease is one of Parkinson's disease, osteoarthritis, stroke, cerebral palsy, multiple sclerosis, and muscular dystrophy.

10. The method of claim 1, wherein providing the output comprises providing the output for an individual's progression based on a plurality of predicted motion evaluation scores over a period of time.

11. The method of claim 1, wherein providing the output comprises providing real-time feedback to a user to adjust the user's motions.

12. The method of claim 1, wherein, the method further comprising:

performing a physics-based simulation based on the set of keypoint trajectories; and training a model based on the physics-based simulation, wherein predicting the motion evaluation score comprises using the trained model to predict the motion evaluation score, wherein the motion evaluation score comprises at least one of muscle activation, muscle fiber length, and joint loads.

13. A non-transitory machine readable medium containing processor instructions for evaluating motion from a video, where execution of the instructions by a processor causes the processor to perform a process that comprises:

identifying a set of one or more keypoint trajectories from a plurality of frames of a video;

providing the set of one or more keypoint trajectories as inputs to an artificial neural network, wherein the artificial neural network is trained using multivariate time series of coordinates of a set of one or more keypoint trajectories extracted from at least one training video, wherein each of the at least one training video is annotated with a true motion evaluation score, wherein the artificial neural network is trained to predict motion evaluation scores based on the multivariate time series of coordinates and the true motion evaluation score of the corresponding training video where the multivariate time series of coordinates are extracted from, wherein the artificial neural network comprises a convolutional neural network having one or more convolutional layers, wherein each of the one or more convolutional layers is configured to:

receive as input, the multivariate time series of coordinates structured as a T×D matrix, where T represents a number of points in a time dimension of the multivariate time series of coordinates, and D represents a depth dimension of the multivariate time series of coordinates; and apply one or more filters of a filter length F to the multivariate time series of coordinates, wherein each filter connects to a local region in the time dimension comprising F consecutive points in the time dimension, and wherein each filter extends through an entirety of the depth dimension such that each filter connects to all D features at each of the F consecutive points in the time dimension;

computing the motion evaluation score based on the set of one or more keypoint trajectories using the artificial neural network; and providing an output based on the motion evaluation score.

14. The non-transitory machine readable medium of claim 13, wherein identifying the set of keypoint trajectories comprises:

identifying a set of keypoints within each of a plurality of frames of the video;

computing each keypoint trajectory of the set of keypoint trajectories based on positions of the keypoint in each frame of the plurality of frames.

15. The non-transitory machine readable medium of claim 13, wherein identifying the set of keypoint trajectories further comprises computing additional features from the identified set of keypoints.

16. The non-transitory machine readable medium of claim 13, wherein the motion evaluation score is one of gait deviation index (GDI), walking speed, cadence, symmetry, gait variability, and stride length.

17. The non-transitory machine readable medium of claim 13, wherein providing the output comprises providing the output for an individual's progression based on a plurality of predicted motion evaluation scores over a period of time.

18. The non-transitory machine readable medium of claim 13, wherein, the non-transitory machine readable medium, wherein the process further comprises:

performing a physics-based simulation based on the set of keypoint trajectories; and training a model based on the physics-based simulation, wherein predicting the motion evaluation score comprises using the trained model to predict the motion evaluation score, wherein the motion evaluation score comprises at least one of muscle activation, muscle fiber length, and joint loads.

* * * * *